(12) United States Patent
Tsygankov

(10) Patent No.: US 7,521,070 B2
(45) Date of Patent: Apr. 21, 2009

(54) AGENT FOR PREVENTING AND CURING PATHOLOGIES STATES ASSOCIATED WITH ENDORPHIN DEFICIENCY IN ORGANISM

(76) Inventor: Vladimir Vladimirovich Tsygankov, d. 72 ul. Lilyakova, s. Khvastovichi Kaluzhskaya obl. (RU) 577298

( * ) Notice: Subject to any disclaimer, the term of this patent is extended or adjusted under 35 U.S.C. 154(b) by 0 days.

(21) Appl. No.: 11/306,576

(22) Filed: Jan. 3, 2006

(65) Prior Publication Data

US 2006/0222717 A1 Oct. 5, 2006

Related U.S. Application Data

(63) Continuation of application No. PCT/RU2004/000057, filed on Feb. 25, 2004.

(30) Foreign Application Priority Data

Mar. 7, 2003 (RU) ............................. 2003119678

(51) Int. Cl.
*A61K 9/00* (2006.01)
*A61K 35/12* (2006.01)
(52) U.S. Cl. ................... 424/520; 424/400; 424/489
(58) Field of Classification Search ............... 424/400, 424/489, 520
See application file for complete search history.

(56) References Cited

U.S. PATENT DOCUMENTS 6,093,421 A * 7/2000 DeLuca et al. ............. 424/543
2003/0228375 A1 * 12/2003 Yegorova ................... 424/643

* cited by examiner

*Primary Examiner*—Ruth A Davis
(74) *Attorney, Agent, or Firm*—Michael M. McGaw; Smith & Hopen, P.A.

(57) ABSTRACT

The inventive powder is made of ossified horns of reindeer and contains 25 pmol/g of endorphins in the form of agent for preventing and treating pathological states associated with endorphin deficiency in organism.

21 Claims, No Drawings

AGENT FOR PREVENTING AND CURING PATHOLOGIES STATES ASSOCIATED WITH ENDORPHIN DEFICIENCY IN ORGANISM

CROSS REFERENCE TO RELATED APPLICATIONS

This application is a continuation of International Application No. PCT/RU2004/000057, filed on Feb. 25, 2004, which claims the benefit of Russian Patent Application No. 20031199678, filed on Mar. 7, 2003.

TECHNICAL FIELD

The present invention relates in general to pharmacology and has particular reference to analgesics.

BACKGROUND ART

Endorphines are essentially protein hormones produced in the hypothalamic brain region, the site of synthesis of said substances being encephalic subcortical nuclei. Endorphines act as neuromediators and perform numerous most diverse functions in organism, the most important of such a variety thereof being a regulatory function of pain sense modality. Being neiromediators, endorphines have an effect on emotional responses by causing one to feel pleasure. Compounds of said class regulate state of hunger, are engaged in memory processes, in organism's response to stress-factors, in emotional disorders and reactions to alcohol, they normalize arterial tension, respiration rate, renal activity, and functioning of the digestive system. It is found experimentally that endorphines promote healing of injured tissues, callus formation in fractures and add to general resistance to sepsis.

In all chronic diseases, secondary effects of stress or depression, declining creative activity there is observed deficiency of endorphines, the causes of which may be most diverse, that is, pathologies of endocrine system, genetic features of organism, infection factor (some viruses inhibit hormonopoiesis of pleasure hormones), dejected mood, perpetual dissatisfaction with oneself and with one's associates.

Normal synthesis of endorphines is deranged also as a result of presence of opiates, e.g., heroin (diacetylmorphine) in organism. Once the opiate introduced into the organism has been destroyed, the level of endorphines therein remains abnormally low, because an euphoria-causative effect of said opiates is due to their being attached to cerebral receptors for endorphines. Abnormally low brain level of endorphines causes physical and emotional pain. To release oneself from pain, the sufferer is compelled to take a great dose of a narcotic, whereby a chemical dependence on opiates is being developed. It is at least a few days should pass until the brain resumes generating endorphines.

One of the methods to increase producing of endorphines is acupuncture which conduces to releasing the available endorphines. Devices that relieve heavy pain by applying a weak electric signal to skin, stimulate generating endorphines. Running or other physical exercises are also causative of increasing release of endorphines under such loads. That is why just regular physical exercises are given such importance in prevention and rehabilitation programs of control of chemical dependence on opiates.

However, said methods are but inadequately effective for therapy of pathologic conditions concerned with deficiency of endorphines in organism.

Known in the present state of the art is a method for increasing the level β-endorphine contained in hypothalamus and hypophysis (cf. "Effect of EMP at the level of β-endorphines in the brain" by V. F. Pavlovski, V. F. Katkov, S. E. Dyakov, said method being a non-pharmacological method of acting upon principal neurochemical mechanisms of CNS functioning forming the basis of nociperception processes, forming an emotional status, stress response, education and memory, drug dependence syndrome and drug addiction.

All endorphines are polypeptides, β-endorphine being a fragment of β-lipotropin, another polypeptide also detectable in hypothalamus and hypophysis. The method consists in that test animals (120 albino rat males each weighing 180-200 g) are exposed to irradiation with a low-energy (specific irradiation energy up to 10 μW/sq.cm) with a pulse-modulated microwave field having characteristics obtained by mathematical simulation on the basis of applying the theory of non-linear pendulums and resonance phenomena to control over biological processes. Upon completing the experiments the test animals are decapitated and the hypothalamus is immediately isolated, the tissue is weighed and rapidly subjected to homogenization with a tenfold volume of 0.2 N HCl solution heated to 95° C. over a boiling water bath. In 15 minutes the tissue specimens are cooled in an ice bath before homogenization and further procedures and β-endorphine is extracted for a two-hour period at t=4° C. and is subjected to centrifuging in a cryocentrifuge at 4500 rpm for 20 minutes. Then the translucent post-centrifugal supernatant fluid is decanted into preprepared test tubes. Then the β-endorphine-containing extracts are frozen and lyophilized by freeze drying. Thereupon the β-endorphine content of the cerebral tissues in the test animals is identified by a high-sensitivity radio-immunoassay method. The fundamental of the method is based on high antiserum sensitivity to β-endorphine. Immediately before the radioassay the specimens are dissolved in a p.1 M borate buffer with pH=8.4 containing 1% bovine albumin. All opiopeptide determination procedures are conducted over an ice bath at t=0 to +2° C. Exposure to the effect of modulated microwave fields leads to a substantial change in the β-endorphine level.

However, the known method is extremely sophisticated technologically and therefore is of little use in therapeutic practice.

A variety of synthetic endorphine analogs were provided having selective effect on one receptors or other. Known in the present state of the art is a powder-like biogenic preparation from ossified deer antlers (cf. RU, A, 2,077,887) which comprises a complex of biologically potent components— amino acids, peptides, lipids, carbohydrates, steroid hormones, fatty acids, organophosphorous compound, as well as a great amount of micro- and macroelements (potassium, calcium, iron, magnesium, zinc, copper, manganine, nickel, tin, chromium, lithium, baryum, and others). It is due a unique composition of the powder ingredients that there is attainable multimodality of treatment effect produced on human organism so as to provide increase in adaptogenic resources which normalizes metabolic effect comprising correction of lipid, protein and carbohydrate metabolism, regulation of redox and hemopoietic processes, increasing immunobiological and body defenses, stimulation of growth and development of osseomuscular tissue, excretion of heavy metals and toxins from organism, and the like.

The present biogenic preparation with preserved natural-origin activity of the starting product has a broad range of pharmacological action which is not yet studied thoroughly.

This in turn prevents its use as a drug for therapy of metabolic disorders and hormonal dysfunction, as well as in narcological practice.

SUMMARY OF INVENTION

It is an object of the present invention to make use of a known medicinal preparation from ossified deer antlers as an agent that normalizes metabolism and hormonal status and is applicable in narcological practice and as an antioxidant.

Said object is accomplished due to the fact that proposed herein is the use of a powder prepared from ossified deer antlers and containing endorphines in an amount of 25 pmole/g, as an medicinal agent for treating and preventing pathologies resulting from deficiency of endorphines in organism. It is due to its revealed properties said agent normalizing metabolism and hormonal status has become applicable in narcological practice, as well as an antioxidant.

DESCRIPTION OF THE PREFERRED EMBODIMENT

The medicinal agent proposed herein is prepared by disintegrating ossified reindeer antlers till obtaining porous particles of the disintegrated product having a dispersity substantially below 0.25 mm, a specific surface of about 100 sq.m/g, and a pore volume of about 3.0 sq.m/g.

The endorphine content is identified by radio-immunoassay technique.

To carry out clinical trials of the proposed pharmaceutical composition, the following groups of human test subjects were constituted:

control group, trial group of human testees administered the agent of the present invention, trial group of human test subjects given pantocrine.

The groups were constituted by two age classes, that is, below 25 and over 30 which was aimed at determining the effect of the agents on dynamics of β-endorphines in various age groups. The groups of testees also comprised surgical subjects for concomitant ascertaining a possibility of applying the agent in the post-operational period, and also one remittent drug addict was included.

Principal standards for selecting human test subjects were cardiovascular system examination findings, such as arterial tension, heart rate, characteristics of PQRST waves, neurologist's medical comment on freedom from syncopal states and on possible psycho-emotional disorders.

Taking due account of standards to be met in selecting the human test subjects, there were included in the groups of said human subjects compulsory military servants (seamen), as well as reserve officers who took treatments at the surgical department of the Naval Hospital.

Additionally, one drug-addict patient was included in the group of test subjects, the functional state of whom complied with the selection standards.

The principal group of test subjects was constituted of eight persons of whom five were compulsory servants, one active-service officer, one reserve officer and one drug-addict patient. The group of test subjects administered pantocrine in a dose of 35 droplets per 100 g water, was also made up of compulsory military servants and active-service military men.

The age characteristics of all test subjects are tabulated below.

For the sake of purity of experimental studies, used as the control group was the main group the members of which were given placebo for four days in succession and from whom blood samples were drawn at different time of day and night so as to avoid the effect of diurnal variations of endorphine concentration in the course of its monitoring. Thereafter the members of the same group were administered the proposed agent in a dose of one or two capsules (0.4 g) once a day in the morning at mealtimes. Doses of the agent are tabulated below. Such an approach provided for adequate interpretation of the results obtained. Blood was withdrawn from the test subjects of the groups who were administered the proposed agent in combination with pantocrine, from a vein in an amount of 6 ml in vacuumized test tubes available from Vacutainer Co. and coated with EDTA for promoting plasma separation, a first blood sampling was effected an hour after the agent administration and two subsequent blood sampling procedures, in 45 minutes each. Such a time interval is necessary in order to better elicit dynamics of endorphines and correlation of endorphine with glucose.

The blood withdrawn from the test subjects was let to settle down in a cooler at +4° C. for 30 minutes, whereupon blood plasma (about 2 ml) was carefully gathered with a pipette, transferred into epindorphs to be frozen there at minus 20° C., wherein the plasma was kept stored until termination of the clinical trials. Thereafter β-endorphine was identified with a set of reagents available from Peninsula Laboratories Inc.

Concurrently with blood sampling for endorphine identification, blood was taken from the same portion to identify glucose with automatic glucometer Accutrend sensor. The results are tabulated below, the unit of measurement being mg %.

As is evident from tables below, administering placebo to the test subjects (Table 1) does not affect the dynamics of β-endorphines, so that their values fall within daily variations and approximate zero.

There stand out from said characteristics those of the test subject #8 on the first and second days of examination, the values of said characteristics being −0.62 and −0.18, respectively, which is in fact the characteristic feature of a remittent drug addict. Arterial tension correspond to that measured before beginning the experiments, and the glucose level corresponds to normal variations depending on taking meals.

A first day of administering the proposed agent revealed but a minor rise in the β-endorphine level in 1 h 30 min after drug administration, whereupon the post-prandial decrease in glucose level rise was observed, the arterial tension dynamics remaining unaffected (Table 2).

A second day of administering the proposed agent revealed a cumulative effect which manifested itself as a considerable rise in the level of β-endorphines and normalized arterial tension in subjects showing arterial hypertension symptoms. Glucose dynamics showed no saltations characteristic of taking meals.

Third and fourth days of the agent administration produced no further stimulating effect on the rise of β-endorphines as compared to the second day of administration. Hence this confirms the fact that the proposed agent adds to the levels of β-endorphines within the limits of physiological norm and may not therefore be assign to euphorigenic agents. A peak level of endorphine is observed in 1 h 30 min after agent administration.

Experimental studies also demonstrate that administration of a double drug dose (i.e., two 0.4 g capsules) of the agent promotes faster rise in the endorphine level (Tables 3 and 5), which may be recommended for debilitated and asthenic patients. It is important to note that administration of a double drug dose did not affect the arterial tension of the test subjects.

The test subjects administered the agent noted amelioration of a general well-being, mood and sleep.

An analysis of the characteristics of the test subjects administered pantocrine demonstrates the endorphine level to rise as well as early as within the first hour following the drug administration but to a less extent as to absolute values than after administering the proposed agent. The endorphine level not only rose faster but dropped also faster, while arterial tension rose considerably which was tolerated especially heavily by hypotonic subjects (Tables 6-9).

The agent of the invention was instituted also to patients who sustained surgery for cavity and vascular operations, wherein there were observed accelerated regenerative processes, amelioration of a general well-being and better dynamics of blood circulation.

The following advantageous features are inherent in the herein-proposed invention.

1. Increase in the β-endorphine level upon the agent administration is effected by virtue of the cumulative effect and manifests itself on the next day after beginning of administration.
2. The effect of increase in the level of endorphines is of a smoothly progressive nature and decreases slowly.
3. Double therapeutic dose of the agent promotes faster increase in the level of endorphines.
4. Duration of the agent administration does not affect the physiological level of endorphines and hence cannot provoke drug habituation.
5. Having a pronounced and persistent effect of increasing the level of β-endorphines, the agent may be recommended as an ancillary medicament in treating drug-addicted patients.
6. As compared to pantocrine the agent of the invention causes a more pronounced increase in the level of β-endorphines and a slower reduction thereof, and unlike pantocrine, does not increase arterial tension.
7. Intake of the agent reduces post-prandial glucose peak levels within the limits of physiological norm and may therefore be recommended to persons predisposed to hyperglycemia.

The proposed agent comprises 25 pmole/g of endorphines, such a content providing high emotional background of organism, freedom from astheno-neurotic and depressive states. The agent in question is a singular one due to its containing naturally occurring endorphines which are capable of producing effect on emotional, psychical and physical regions of human organism, while its capabilities to correct the aforementioned pathologies are unique.

Efficient use of the proposed agent is also corroborated by the examples that follow.

EXAMPLE 1

Male patient, 30, heroin addicted for a prolonged period of time; has passed a monthly course of multimodality therapy comprising administering the proposed agent in a dose of 0.8 g twice a day, hypnosis and psychotherapy, the result being a clearly pronounced positive effect.

EXAMPLE 2

Female patient, 17, suffering from mild depression, has been administered the proposed agent in a daily dose of 0.8 g for a month in conjunction with electrosleep, the result being stable positive emotional disposition.

EXAMPLE 3

Male patient, 50, has sustained hepatitis B; administered the proposed agent in a dose of 0.8 g twice a day to prevent the morbid process from taking a chronic form; notes freedom from asthenic and dyspeptic syndrome and normal level of transaminases.

EXAMPLE 4

Male patient, 20, heroin addict in the past; administered the proposed agent in courses of 0.8 g twice for a two-month period, the courses being repeated every two months. Stable remission persists.

INDUSTRIAL APPLICABILITY

The present invention is successfully applicable for correction of metabolic and hormonal dysfunction and in multimodality therapy of alcohol and drug addiction.

TABLE 1

Dynamics of characteristics in the control group of test subjects

| Nos | Year of birth | Arterial tension | Glucose | Endorphine 1 | Arterial tension | Glucose - | Endorphine 2 | Arterial tension | Glucose | Nos | Arterial tension. | Glucose | Endorphine 4 |
|---|---|---|---|---|---|---|---|---|---|---|---|---|---|
| 1 | 1983 | 120/70 | 86 | 0.18 | 130/80 | 137 | 0.15 | 125/70 | 91 | 0.18 | 120/70 | 87 | 0.1 |
| 2 | 1981 | 105/70 | 80 | −0.1 | 135/75 | 124 | −0.01 | 130/75 | 103 | 0.10 | 125/75 | 80 | 0.01 |
| 3 | 1983 | 110/80 | 75 | 0.11 | 130/80 | 118 | 0.09 | 125/80 | 87 | 0.10 | 125/80 | 105 | 0.1 |
| 4 | 1961 | 125/80 | 96 | −0.01 | 120/75 | 120 | −0.02 | 120/80 | 98 | −0.01 | 120/80 | 90 | 0.01 |
| 5 | 1984 | 120/80 | 83 | 0.02 | 120/80 | HO | 0.11 | 120/80 | 105 | 0.18 | 130/70 | 98 | 0.09 |
| 6 | 1983 | 120/70 | 72 | 0 | 130/75 | 133 | 0.03 | 125/75 | 96 | 0.06 | 130/70 | 87 | 0.05 |
| 7 | 1946 | 135/80 | 97 | 0.05 | 130/90 | 115 | 0.07 | 130/80 | 102 | −0.08 | 130/80 | 91 | 0.01 |
| 8 | 1978 | 150/100 | 81 | −0.62 | 150/80 | 136 | −0.18 | 140/80 | 98 | 0.17 | 145/85 | 87 | 0.15 |

TABLE 2

$1^{st}$ day
Dynamics of characteristics in the group of test subjects administered the proposed agent

| Nos | Year of birth | Dose | Arterial tension | Glucose | Endorphine 1 | Arterial tension | Glucose | Endorphine 2 | Arterial tension | Glucose | Endorphine 3 |
|---|---|---|---|---|---|---|---|---|---|---|---|
| 1 | 1963 | 1 | 125/70 | 85 | 0.2 | 130/80 | 96 | 0.22 | 125/70 | 91 | 0.20 |
| 2 | 1981 | 1 | 120/70 | 75 | 0.1 | 135/75 | 87 | 0.11 | 128/70 | 80 | 0.10 |
| 3 | 1983 | 1 | 125/70 | 80 | 0.12 | 130/80 | 90 | 0.14 | 120/75 | 78 | 0.10 |
| 4 | 1961 | 2 | 125/80 | 84 | 0.11 | 120/75 | 94 | 0.2 | 125/75 | 82 | −0.01 |
| 5 | 1984 | 2 | 125/80 | 83 | 0.05 | 120/80 | 78 | 0.21 | 120/80 | 75 | 0.20 |
| 6 | 1983 | 2 | 120/70 | 75 | 0.1 | 130/75 | 81 | 0.19 | 125/75 | 80 | 0.06 |

TABLE 2-continued

1st day
Dynamics of characteristics in the group of test subjects administered the proposed agent

| Nos | Year of birth | Dose | Arterial tension | Glucose | Endorphine 1 | Arterial tension | Glucose | Endorphine 2 | Arterial tension | Glucose | Endorphine 3 |
|---|---|---|---|---|---|---|---|---|---|---|---|
| 7 | 1946 | 1 | 135/80 | 78 | 0.02 | 130/90 | 85 | 0.14 | 135/80 | 74 | −0.06 |
| 8 | 1947 | 1 | 145/100 | 82 | −0.1 | 150/90 | 94 | 0.15 | 140/80 | 81 | 0.28 |

TABLE 3

2nd day
Dynamics of characteristics in the group of test subjects administered the proposed agent

| Nos | Year of birth | Dose | Arterial tension | Glucose | Endorphine 1 | Arterial tension | Glucose | Endorphine 2 | Arterial tension | Glucose | Endorphine 3 |
|---|---|---|---|---|---|---|---|---|---|---|---|
| 1 | 1983 | 1 | 125/70 | 81 | 0.33 | 135/70 | 93 | 0.37 | 130/75 | 87 | 0.35 |
| 2 | 1981 | 1 | 125/75 | 74 | 0.33 | 110/70 | 60 | 0.4 | 125/70 | 91 | 0.43 |
| 3 | 1983 | 1 | 135/80 | 95 | 0.37 | 130/85 | 76 | 0.41 | 130/85 | 87 | 0.39 |
| 4 | 1961 | 2 | 130/80 | 89 | 0.49 | 120/70 | 98 | 0.5 | 120/80 | 75 | 0.49 |
| 5 | 1984 | 2 | 120/80 | 84 | 0.42 | 120/80 | 86 | 0.42 | 120/80 | 86 | 0.38 |
| 6 | 1983 | 2 | 130/70 | 78 | 0.37 | 130/75 | 85 | 0.32 | 125/70 | 82 | 0.30 |
| 7 | 1946 | 1 | 120/80 | 82 | 0.39 | 130/85 | 91 | 0.38 | 135/75 | 73 | 0.42 |
| 8 | 1947 | 1 | 130/78 | 91 | 0.33 | 130/85 | 89 | 0.39 | 135/78 | 79 | 0.41 |

TABLE 4

3rd day
Dynamics of characteristics in the group of test subjects administered the proposed agent

| Nos | Year of birth | Dose | Arterial tension | Glucose | Endorphine 1 | Arterial tension | Glucose | Endorphine 2 | Arterial tension | Glucose | Endorphine 3 |
|---|---|---|---|---|---|---|---|---|---|---|---|
| 1 | 1983 | 1 | 120/70 | 85 | 0.37 | 125/70 | 84 | 0.39 | 125/70 | 84 | 0.37 |
| 2 | 1981 | 1 | 120/75 | 78 | 0.35 | 115/70 | 76 | 0.39 | 120/70 | 90 | 0.45 |
| 3 | 1983 | 1 | 130/80 | 95 | 0.4 | 120/75 | 78 | 0.43 | 125/80 | 85 | 0.40 |
| 4 | 1961 | 2 | 125/80 | 85 | 0.52 | 125/70 | 81 | 0.51 | 120/80 | 76 | 0.45 |
| 5 | 1984 | 2 | 120/80 | 80 | 0.48 | 120/80 | 64 | 0.43 | 120/80 | 80 | 0.42 |
| 6 | 1983 | 2 | 130/75 | 83 | 0.42 | 130/70 | 87 | 0.39 | 130/75 | 81 | 0.33 |
| 7 | 1946 | 1 | 130/80 | 76 | 0.38 | 130/80 | 90 | 0.37 | 135/80 | 74 | 0.39 |
| 8 | 1947 | 1 | 135/80 | 87 | 0.35 | 125/80 | 79 | 0.41 | 125/80 | 80 | 0.42 |

TABLE 5

4th day
Dynamics of characteristics in the group of test subjects administered the proposed agent

| Nos | Year of birth | Dose | Arterial tension | Glucose | Endorphine 1 | Arterial tension | Glucose | Endorphine 2 | Arterial tension | Glucose | Endorphine 3 |
|---|---|---|---|---|---|---|---|---|---|---|---|
| 1 | 1983 | 1 | 118/70 | 87 | 0.39 | 120/70 | 83 | 0.41 | 120/75 | 81 | 0.39 |
| 2 | 1981 | 1 | 120/70 | 75 | 0.41 | 120/70 | 75 | 0.43 | 120/80 | 96 | 0.44 |
| 3 | 1983 | 1 | 115/70 | 94 | 0.38 | 120/75 | 73 | 0.42 | 125/75 | 84 | 0.39 |
| 4 | 1961 | 2 | 120/70 | 80 | 0.49 | 125/80 | 80 | 0.51 | 120/80 | 84 | 0.47 |
| 5 | 1984 | 2 | 120/80 | 87 | 0.46 | 120/80 | 88 | 0.44 | 120/80 | 81 | 0.43 |
| 6 | 1983 | 2 | 130/70 | 82 | 0.48 | 125/70 | 85 | 0.41 | 130/80 | 83 | 0.38 |
| 7 | 1946 | 1 | 130/75 | 75 | 0.37 | 130/80 | 79 | 0.39 | 135/75 | 80 | 0.35 |
| 8 | 1947 | 1 | 135/80 | 86 | 0.38 | 125/80 | 81 | 0.39 | 130/80 | 80 | 0.34 |

TABLE 6

1st day
Dynamics of characteristics in the group of test subjects administered the Pantocrine

| Nos | Year of birth | Dose | Arterial tension | Glucose | Endorphine 1 | Arterial tension | Glucose | Endorphine 2 | Arterial tension | Glucose | Endorphine 3 |
|---|---|---|---|---|---|---|---|---|---|---|---|
| 1 | 1973 | 1 | 110/70 | 84 | 0.01 | 150/90 | 110 | 0.23 | 140/80 | 81 | 0.31 |
| 2 | 1961 | 1 | 120/70 | 80 | −0.01 | 145/80 | 98 | 0.19 | 135/80 | 96 | 0.28 |
| 3 | 1962 | 1 | 115/70 | 87 | 0 | 140/90 | 120 | 0.22 | 130/75 | 84 | 0.12 |
| 4 | 1972 | 1 | 115/60 | 79 | 0.02 | 150/80 | 95 | 0.26 | 140/80 | 84 | 0.36 |
| 5 | 1964 | 1 | 120/80 | 90 | −0.01 | 140/80 | 102 | 0.11 | 130/80 | 81 | 0.23 |

TABLE 7

2$^{nd}$ day
Dynamics of characteristics in the group of test subjects administered the Pantocrine

| Nos | Year of birth | Dose | Arterial tension | Glucose | Endorphine 1 | Arterial tension | Glucose | Endorphine 2 | Arterial tension | Glucose | Endorphine 3 |
|---|---|---|---|---|---|---|---|---|---|---|---|
| 1 | 1973 | 1 | 120/70 | 94 | 0.19 | 150/80 | 92 | 0.31 | 140/80 | 97 | 0.21 |
| 2 | 1961 | 1 | 12/70 | 85 | 0.23 | 140/80 | 104 | 0.33 | 135/80 | 102 | 0.16 |
| 3 | 1962 | 1 | 125/70 | 95 | 0.27 | 135/75 | 112 | 0.35 | 130/75 | 94 | 0.12 |
| 4 | 1972 | 1 | 120/70 | 93 | 0.29 | 145/80 | 98 | 0.37 | 140/80 | 101 | 0.17 |
| 5 | 1964 | 1 | 125/75 | 101 | 0.31 | 140/75 | 103 | 0.34 | 130/80 | 95 | 0.19 |

TABLE 8

3$^{rd}$ day
Dynamics of characteristics in the group of test subjects administered the Pantocrine

| Nos | Year of birth | Dose | Arterial tension | Glucose | Endorphine 1 | Arterial tension | Glucose | Endorphine 2 | Arterial tension | Glucose | Endorphine 3 |
|---|---|---|---|---|---|---|---|---|---|---|---|
| 1 | 1973 | 1 | 130/75 | 114 | 0.24 | 145/80 | 97 | 0.31 | 150/80 | 87 | 0.22 |
| 2 | 1961 | 1 | 125/70 | 97 | 0.28 | 135/80 | 102 | 0.33 | 140/80 | 94 | 0.21 |
| 3 | 1962 | 1 | 130/70 | 93 | 0.33 | 140/75 | 110 | 0.35 | 140/75 | 99 | 0.19 |
| 4 | 1972 | 1 | 125/70 | 108 | 0.32 | 140/80 | 96 | 0.37 | 135/80 | 114 | 0.21 |
| 5 | 1964 | 1 | 130/70 | 120 | 0.29 | 145/75 | 102 | 0.34 | 135/80 | 96 | 0.25 |

TABLE 9

4$^{th}$ day
Dynamics of characteristics in the group of test subjects administered the Pantocrine

| Nos | Year of birth | Dose | Arterial tension | Glucose | Endorphine 1 | Arterial tension | Glucose | Endorphine 2 | Arterial tension | Glucose | Endorphine 3 |
|---|---|---|---|---|---|---|---|---|---|---|---|
| 1 | 1973 | 1 | 130/70 | 98 | 0.26 | 145/80 | 104 | 0.34 | 150/80 | 98 | 0.21 |
| 2 | 1961 | 1 | 130/75 | 86 | 0.31 | 140/80 | 112 | 0.31 | 140/80 | 104 | 0.17 |
| 3 | 1962 | 1 | 140/75 | 91 | 0.32 | 140/70 | 104 | 0.36 | 145/80 | 112 | 0.12 |
| 4 | 1972 | 1 | 130/70 | 120 | 0.34 | 140/75 | 93 | 0.38 | 140/80 | 105 | 0.19 |
| 5 | 1964 | 1 | 135/80 | 91 | 0.33 | 145/70 | 114 | 0.31 | 135/80 | 101 | 0.24 |

What is claimed is:

1. A method of treating a disease characterized by a deficiency of endorphins in a subject comprising the step of administering to the subject in need of such treatment a therapeutically effective amount of a composition containing an ossified antler preparation.

2. The method according to claim 1 wherein the antler is an ossified deer antler.

3. The method according to claim 1 wherein a range of 400 mg to 1.6 g of the ossified deer antler preparation is administered daily.

4. The method according to claim 3 wherein the concentration of endorphin in the antler preparation is about 25 pmole/g.

5. The method according to claim 1 wherein the endorphin deficiency is resulting from the cessation of the administration of an addictive substance to the subject.

6. The method according to claim 5 wherein the addictive substance is selected from the group consisting of a drug and alcohol.

7. The method according to claim 1 wherein the endorphin deficiency is resulting from the cessation of opioid usage by the subject.

8. The method according to claim 1 wherein the antler preparation is administered in capsular or tablet form.

9. The method according to claim 1 wherein the antler preparation is administered in the morning contemporaneously with a meal.

10. The method according to claim 1 wherein the composition consists essentially of ossified antler.

11. The method according to claim 1 wherein the antler component of the administered composition consists essentially of ossified antler.

12. A method of raising the level of beta-endorphins in a subject comprising the step of administering to the subject in need of such treatment a therapeutically effective amount of a composition containing an ossified antler preparation.

13. The method according to claim 12 wherein the antler is an ossified deer antler.

14. The method according to claim 12 wherein the composition consists essentially of ossified antler.

15. The method according to claim 12 wherein a range of 400 mg to 1.6 g of the ossified deer antler preparation is administered daily.

16. The method according to claim 12 wherein the concentration of endorphin in the antler preparation is about 25 pmole/g.

17. The method according to claim 12 wherein the endorphin deficiency is resulting from the cessation of the administration of an addictive substance to the subject.

18. The method according to claim 12 wherein the endorphin deficiency is resulting from the cessation of opioid usage by the subject.

19. The method according to claim 12 wherein the antler component of the administered composition consists essentially of ossified antler.

20. A method of treating a deficiency of endorphins in a subject comprising the step of administering to the subject in need of such treatment a therapeutically effective amount of a composition containing an ossified antler preparation.

21. The method according to claim 20 wherein the composition consists essentially of ossified antler.

* * * * *